(12) United States Patent
Bragger

(10) Patent No.: US 10,064,916 B2
(45) Date of Patent: Sep. 4, 2018

(54) TREATMENT METHOD FOR MICROBIAL INFECTION

(71) Applicant: DEC International NZ Limited, Hamilton (NZ)

(72) Inventor: Judith Mary Bragger, Hamilton (NZ)

(73) Assignee: DEC International NZ Limited, Hamilton (NZ)

( * ) Notice: Subject to any disclaimer, the term of this patent is extended or adjusted under 35 U.S.C. 154(b) by 0 days.

(21) Appl. No.: 14/018,280

(22) Filed: Sep. 4, 2013

(65) Prior Publication Data

US 2014/0065161 A1 Mar. 6, 2014

Related U.S. Application Data

(62) Division of application No. 12/304,108, filed as application No. PCT/NZ2007/000144 on Jun. 8, 2007, now abandoned.

(30) Foreign Application Priority Data

Jun. 8, 2006 (NZ) ........................ 547859

(51) Int. Cl.
| | | |
|---|---|---|
| *A61K 38/17* | (2006.01) | |
| *A61K 35/20* | (2006.01) | |
| *A61K 38/40* | (2006.01) | |
| *A61K 38/44* | (2006.01) | |
| *A61K 45/06* | (2006.01) | |
| *A61K 38/18* | (2006.01) | |
| *A61K 38/19* | (2006.01) | |
| *A61K 38/30* | (2006.01) | |
| *A61K 38/54* | (2006.01) | |

(52) U.S. Cl.
CPC .......... *A61K 38/1732* (2013.01); *A61K 35/20* (2013.01); *A61K 38/1841* (2013.01); *A61K 38/1891* (2013.01); *A61K 38/19* (2013.01); *A61K 38/30* (2013.01); *A61K 38/40* (2013.01); *A61K 38/44* (2013.01); *A61K 38/54* (2013.01); *A61K 45/06* (2013.01); *C12Y 111/01007* (2013.01)

(58) Field of Classification Search
None
See application file for complete search history.

(56) References Cited

U.S. PATENT DOCUMENTS

| 4,377,569 A | * | 3/1983 | Plymate ..................... 424/157.1 |
| 4,436,658 A | | 3/1984 | Peyrouset et al. |
| 5,146,647 A | | 9/1992 | Blase et al. |
| 5,516,675 A | * | 5/1996 | Uchida et al. ................ 435/192 |
| 5,866,418 A | | 2/1999 | Ballard et al. |
| 5,976,597 A | | 11/1999 | Takada et al. |
| 6,544,498 B1 | * | 4/2003 | Takada ................... A23G 4/126 424/49 |
| 2003/0013661 A1 | * | 1/2003 | Takada et al. .................. 514/21 |
| 2007/0027119 A1 | * | 2/2007 | Ahmed .................. A01N 31/02 514/159 |

FOREIGN PATENT DOCUMENTS

| EP | 0622071 | * | 11/1994 |
| EP | 0518448 B1 | | 9/1997 |
| EP | 1068871 A1 | | 1/2001 |
| EP | 0704218 B1 | | 3/2003 |
| RU | 2155048 | * | 8/1999 |
| RU | 2155048 C1 | * | 8/2000 |
| WO | WO 2004/056193 | | 7/2004 |

OTHER PUBLICATIONS

Kai et al. Journal of Veterinary Medical Science 64:10,873-878, 2002.*
Marshall et al. Journal of Dairy Research, 53, pp. 507-514, 1986.*
Wheeler et al. Animal (2012), 6:3, pp. 415-422.*
Losnedhal et al. Antimicrobial Factors in Milk. Aug. 5, 1998. Obtained from http://livestocktrail.illinois.edu/dairynet/paperDisplay.cfm?ContentID=229 on May 18, 2015.*
Hahn et al. Journal of Chromatography A, 795 (1998) 277-287.*
Badet, Josette. Angiogenin In: Bikfalvi A, ed. Encyclopaedic of Vascular Biology and Pathology. Berlin Heidelberg:Springer-Verlag, 2000:16:29.*
Ye et al. Biochemical and Biophysical Research Communications 263, 187-191, 1999.*
Clare et al. Biodefense Properties of Milk: The Role of Antimicrobial Proteins and Peptides. Current Pharmaceutical Design, 2003,91239-1255.*
Toba et al. Bone vol. 27, No. Sep. 3, 2000:403-408.*
Uniprot accession # P30922-CH#L1_Bovin for Chitinase like protein bovine Jul. 1, 1993.*
Marshall, Keri. Therapeutic Applications of Whey Protein. Alternative Medicine Review 9.2 (Jun. 2004):136(21).*
Nair et al. J Dairy Sce. 88: 3488-3495.*
Garton et al. J. Lipid Research, Jul. 1963 vol. 4, No. 3.*
Loesche, Walter J. Microbiology of Dental Decay and Periodontal Disease: In Medical Microbiology. Baron S, editor. 4th Edition, 1996: disclose that periodontal disease is caused by gram negative bacteris such as P. gingivalis or T. denticola or A. acitnomycetemcomitans.*
Aoe, S., et al. A controlled trial of the effect of milk basic protein (MBP) supplementation on bone metabolism in healthy menopausal women. Osteoporosis International 2005; 16:2123-8.
Cornish J, Lactoferrin promotes bone growth Biometals. Jun. 2004;17(3):331-5.
Dorit Naot; Andrew Grey; Ian R. Reid; Jillian Cornish Lactoferrin—A Novel Bone Growth Factor Clin Med Res. May 2005; 3(2): 93-101.

(Continued)

*Primary Examiner* — Oluwatosin A Ogunbiyi
(74) *Attorney, Agent, or Firm* — Knobbe Martens Olson & Bear LLP

(57) ABSTRACT

A treatment composition for treating or preventing bovine mastitis, the treatment composition characterized in that it includes at least two components which have an isoelectric point of or above substantially 6.8 and is extracted from milk, or a milk derived substance.

11 Claims, 12 Drawing Sheets

(56) References Cited

OTHER PUBLICATIONS

Yamamura, J., et al. Milk basic protein (MBP) increases radial bone mineral density in healthy adult women. Bioscience, Biotechnology, and Biochemistry 2002; 66(3):702-4.
Clare et al., Bioactive Milk Peptides: A Prospectus, J Dairy Sci., 2000, vol. 83, pp. 1187-1195.
Fang et al., Decreased Growth of *Streptococcus uberis* in Milk from Mammary Glands of Cows Challenged with the Same Mastitis Pathogen, J. Vet. Med, 1998, vol. 45, pp. 539-549.
Strydom et al., An angiogenic protein from bovine serum and milk: Purification and primary structure of agiogenin-2, Eur. J. Biochem., 1997, vol. 247, pp. 535-544.
Rao et al., Protein Fraction in Human Milk: Part II—Isolation & Characterization of Basic Protein from Human Milk & the Lytic Activity of Milk Samples, Indian Journal of Biochemistry & Biophysics, 1973, vol. 10, pp. 87-90.
Reiter et al., Bacterial inhibitors in milk and other biological fluids, Nature, vol. 216, Oct. 28, 1967, p. 328-330.

\* cited by examiner

TREATMENT METHOD FOR MICROBIAL INFECTION

RELATED APPLICATIONS

This application is a divisional of U.S. patent application Ser. No. 12/304,108, filed Sep. 28, 2010, which is the U.S. National Phase of PCT International Application No. PCT/NZ07/00144 which claims priority under 35 U.S.C. § 119(a)-(d) from New Zealand Patent Application No. 547859, filed Jun. 8, 2007.

TECHNICAL FIELD

This invention relates to a treatment method.

In particular it relates to a method of treating bovine mastitis, and a method of producing the treatment composition.

BACKGROUND ART

Mastitis is an inflammatory disease of the mammary gland of a mammal.

The inflammation is the result of infection by any of a multitude of bacteria, mycoplasmas, yeast and fungi. The range of different organisms that can cause mastitis and their varying susceptibilities to antibiotics presents the greatest challenge in the treatment and prevention of mastitis in dairy cows.

Bovine mastitis may be caused by Gram negative bacteria such as *Escherichia coli, Klebsiella* species and *Enterbacter* species, or by Gram-positive bacteria such as *Staphylococcus aureus, Enterococci* species, and *Streptococci* such as *Streptococcus uberis, Streptococcus agalactiae* and *Streptococcus dysgalactiae*, and by *Mycoplasma bovis*.

Bacterial infection via the teats is the most common cause of mastitis. There is an increased risk of intra-mammary infection during the dry period because the teat is no longer protected by the flow of milk through the teat. Milk is known to have a natural anti-microbial action. Dairy cows are bred for increased milk production. There is a negative correlation between milk production capacity and resistance to mastitis, attributable in part to the increased metabolic stress associated with the synthesis of milk. The large volume of milk may also overwhelm the natural defense systems in the udder.

The teat canal plays a large part in preventing infections in the teat and udder such as mastitis. The teat canal has several anatomical and physiological features that serve as a barrier to penetration by bacterial.

The normal teat canal represents a physical barrier to the penetration of bacteria and is the single most important barrier to udder infection. Essentially, there are three main defense mechanisms offered by the teat canal: adsorptive capacity of keratin for bacteria, desiccation of the canal lumen and desquamation of the keratin lining during milk flow.

Besides being a physical barrier, the canal also contains long chain fatty acids produced by continuous keratinization of epithelial cells that are antibacterial, and a protein called ubiquitin that acts as a general antiseptic against incoming bacteria. In a healthy teat, the keratin plug mechanically traps debris and bacteria and absorb them within the extracellular lipid film (Bramley and Dodd, 1984).

Epithelial desquamation and milk flow during lactation limit bacterial colonization in the teat canal. However, at the beginning of the dry period when milk production ceases, bacteria are able to colonize the teat canal, and multiply and subsequently infect the mammary gland.

Teat seal formulations are currently available—however it is not known for these to include milk components, such as lactoferrin or lactoperoxidase. These form a physical barrier to the teat canal, thereby preventing entry of microorganisms during the dry period. Some of these formulations include antibiotics, or chemicals known to have anti-microbial activity. Antibiotics require withholding periods which can increase the time and effort required by the farmer, and may not effectively target the pathogens causing the mastitis.

The primary treatment for bovine mastitis is the administration of antibiotics such as penicillin. Antibiotics belonging to the penicillin and cephalosporin family are most effective against Gram-positive bacteria and have poor or strain-dependent activity against Gram-negative pathogens. A study in Poland (Malinowski et al, 2002) found that out of 517 strains of *Staphylococcus aureus* from subclinical and clinical mastitis, more than 60% were resistant to penicillin and ampicillin, more than 40% were resistant to amoxicillin, 30% were resistant to cephalosporin, 26% were resistant to tetracycline or erythromycin and 54-55% were resistant to lincomycin. Aminoglycosides have a broader spectrum of activity but are not effective against bacteria with rapid growth.

Bovine mastitis is of considerable economic significance to the dairy industry. This is particularly due to the following:

the high cost of the treatment, the loss of milk during the infected period, and subsequent withholding period following the use of antibiotics. If antibiotics are found in the milk supplied to a dairy company, the whole batch may need to be discarded, and the farmer may face large penalties.

cross-contamination within the herd long-term loss of milk over the life of the animal due to decreased mammary capacity A number of milk components have previously been isolated, purified and discussed in relation to use to prevent or treat mastitis, these include:

Lactoferrin (Lf), a glycoprotein which is present in mammary gland secretion and many other exocrine secretions of mammals, Lf is secreted predominately by surface epithelia into the mucosal environment. Lactoferrin is a multifunctional protein that has antibacterial, antifungal, antiviral, antitumour, anti-inflammatory, and immunoregulatory properties Lf is produced at high levels in nasal and tracheal passages, and in gastric, genital and opthalmic secretions. Lf is also produced at high levels in neutrophils where it is stored in secondary granules and released during inflammation.

The mechanism by which Lf inhibits microbial growth has not been fully elucidated. Its antimicrobial and anti-inflammatory effects are believed to be as a result of a number of different actions or functions of Lf.

The highly basic N terminal region of bovine lactoferrin is essential for antimicrobial activity. The 25 N-terminal amino acids may be removed by proteases to form Lactoferricin (Lfcin). These proteases may be naturally occurring in milk or serum, and many micro-organisms produce proteases. LFcin is up to a 1000 fold more effective against some micro-organisms than intact lactoferrin. Lfcin has been shown to inhibit a diverse range of microorganisms such as gram-negative bacteria, gram-positive bacteria, yeast, filamentous fungi, and parasitic protozoa, including some antibiotic-resistant pathogens.

Lf binds to lipopolysaccharide. When Gram-negative bacteria are killed by the natural defense system of the animal or by antimicrobial agents the release of lipopolysaccharide from the cell walls of the bacteria provokes an inflammatory response. One of the primary actions of Lf therefore is to bind the LPS and prevent the inflammatory response. Lf also displays an immunomodulatory role by binding with high affinity to bacterial endotoxin, thus protecting against endotoxin lethal shock.

Lf is also an iron binding glycoprotein. Most micro organisms need iron for growth and therefore Lf has the potential to inhibit the growth of bacteria and even kill them by depriving them of iron. The effectiveness of the antibacterial activity of Lf depends on the iron requirement of the organism, being availability of exogenous iron, and the concentration and degree of iron saturation of Lf. It has been shown that natural Lf is bacteriostatic against a wide range of micro organisms, including gram negative bacteria with high iron requirements, and some gram positive organisms such as *Staphylococcus aureus* which is a major mastitis pathogen.

Current commercial applications of bovine Lf include infant formulas, fermented milks, nutritional iron supplements, chewing gums, immune-enhancing nutraceuticals, cosmetic formulas and feed and pet care supplements.

The increased concentrations of endogenous Lf in milk during the dry period, and the bacteriostatic and bactericidal effects of exogenous Lf have lead to research in the use of Lf for treating or preventing mastitis. This research has in the past focused on increasing the purity and extraction rates of Lf to increase the beneficial effect.

Another milk component is Lactoperoxidase (Lp), a protein present in the mammary gland secretion and many other exocrine secretions of mammals.

The Lactoperoxidase system consists of three components—lactoperoxidase, thiocyanate and hydrogen peroxide, which are all present in fresh milk. Lp catalyses the oxidation of thiocyanate by peroxide and generates intermediate products with antibacterial properties. Mammalian cells are not affected by these oxidation products and the Lp system may actually protect cells against the toxic effects of hydrogen peroxide. Thiocyanate is present in the mammary, salivary and thyroid glands and their secretions, in synovial, cerebral, cervical and spinal fluids, in lymph and plasma, and in organs such as stomach and kidney. Hydrogen peroxide, the third component of the Lactoperoxidase system is not normally detected in milk. It may be generated endogenously by polymorphonuclear leucocytes in the process of phagocytosis. *Lactobacilli, lactococci* and *streptococci* produce sufficient hydrogen peroxide under aerobic conditions to activate the Lp system.

When provided with the substrate thiocyanate, Lp generates the biocidal compound hypothiocyanite ($OSCN^-$). Halides also act as substrate for Lp. Kussendrager and Hooijdonk (2000) state that oxidation of even small amounts of $I^-$ might be significant regarding antimicrobial action because the $LP-H_2O_2-SCN^-$ system is primarily bacteriostatic whereas the $LP-H_2O_2-I^-$ system is bactericidal.

The Lactoperoxidase system has bacteriostatic or bactericidal activity on a variety of susceptible micro-organisms including bacteria, fungi and viruses.

Lp has been used for the preservation of raw milk during storage and transportation, to extend the shelf-life of dairy products, as a preservative in cosmetics and pharmaceuticals. A number of oral hygiene products, such as mouthwashes and toothpaste containing Lp are commercially available. Uses include wound treatment and opthalmic solutions.

Immunoglobulins are an important component of milk and provide passive protection to the suckling young. Although they are not strongly cationic some immunoglobulins, IgG, IgM, IgA and polymeric immunoglobulin receptor (PIGR) are captured by cation exchange. Immunoglobulins are important in the first line of defence against foreign invaders. Immunoglobulins bind to micro-organisms and thus opsonise them so that they are more easily recognized by phagocytic cells.

A number of proteins and peptides belonging to the ribonuclease superfamily have been identified in milk. Some of these have been purified and shown to have antiviral and anti-microbial activity. They are variously described as RNase5, angiogenin 1, angiogenin 2 and lactogenin.

Angiogenin is a small polypeptide that is implicated in the formation of new blood vessels. Angiogenin is unique among the many proteins that are involved in angiogenesis in that it is also an enzyme with an amino acid sequence 33% identical to that of bovine pancreatic ribonuclease (RNase A). Moreover, although Ang has the same general catalytic properties as RNase A—it cleaves preferentially on the 3' side of pyrimidines and follows a transphosphorylation/hydrolysis mechanism—its activity differs markedly both in magnitude and in specificity.

Although angiogenin contains counterparts for the key catalytic residues of bovine pancreatic RNase A, it cleaves standard RNase substrates $10_5$-$10_6$ times less efficiently than does RNase A. Despite this apparent weakness, the enzymatic activity of Ang appears to be essential for biological activity: replacements of important active site residues invariably diminish ribonuclease and angiogenesis activities in parallel, and a substitution that increases enzymatic activity also enhances angiogenic potency (See "Angiogenin" in Wikipedia, May 2006).

The concentration in milk of a number of proteins and peptides increases rapidly in response to trauma or infection. These are known as acute phase proteins (APP) and include lactoferrin, the ribonucleases, N-acetyl glucosaminidase, serum amyloid A, β Defensin and lysozyme.

Work in the dairy field on developing treatment or preventative uses of Lf and Lp have previously been focused towards obtaining more pure and concentrated forms of these proteins from milk.

For example WO 03/002090 discloses the use of Lf, or pharmaceutically acceptable salts thereof to cows to provide a smooth transition of the mammary gland from a lactation period to a dry period. WO 03/002090 discloses the use of small volumes (preferably 100-250 mg/udder) of Lf in ointment or liquid form.

The use of extracted and purified Lf or Lp, or other milk components for the treatment or prevention of mastitis require the extraction, isolation and purification of more concentrated and pure versions of these components.

Unfortunately extraction and purification methods can be time consuming, expensive and hard to develop and implement, especially on a large scale.

Also, the pure products are not fully effective in treating infection.

It is therefore desirable to have available a natural product which is quick and easy to produce which effectively prevents or treats bovine mastitis.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided a treatment composition for treating or preventing bovine mastitis, the treatment composition characterised in that it includes at least two components which have an isoelectric point of or above substantially 6.8 and is extracted from milk, or a milk derived substance.

Throughout this specification the treatment composition will be referred to as a cationic fraction.

Throughout this specification the term cationic fraction should be taken as meaning a fraction of milk, being cationic components that bind to cation exchange media. The cationic fraction should be taken to include any component of milk which has an isoelectric point of or above substantially 6.8.

In a preferred embodiment the treatment composition may be a cationic fraction which includes at least lactoferrin, lactoperoxidase and angiogenin.

In one preferred embodiment the cationic fraction may have the following characteristics:
a molecular weight distribution of 3,000-80,000 Daltons by SDS-PAGE,
isoelectric points of 6.8-11,
the main components are lactoferrin, lactoperoxidase and angiogenin.

In a preferred embodiment, as well as the lactoferrin, lactoperoxidase and angiogenin the cationic fraction may include a mixture of cationic peptides.

In a preferred embodiment, as well as the lactoferrin, lactoperoxidase and angiogenin the cationic fraction may include at least one of the following: N-acetyl glucosaminidase, serum amyloid A, β Defensin or lysozyme.

In a preferred embodiment the cationic fraction shall be taken as meaning an extract which contains a number of milk micro-components, specifically lactoferrin, lactoperoxidase, angiogenin, N-acetyl glucosaminidase, serum amyloid A, β Defensin or lysozyme.

In a preferred embodiment the cationic fraction may also include lactoferricin, a fragment of lactoferrin that is claimed to be 10-1000 times more anti-microbial than intact lactoferrin. In some embodiments the cationic fraction may undergo further processing to enhance the content or ratio of lactoferricin.

In a preferred embodiment the cationic fraction may also include CLP-1 (chitinase-like protein), or at least one lysozyme-like component.

In a preferred embodiment the cationic fraction may also include at least one immunoglobulin. Immunoglobulin(s) which could be expected to be present may include type G, A, M, E or D immunoglobulin.

In a preferred embodiment the cationic fraction may include at least one micro-component.

Throughout this specification the term micro-components should be taken as meaning bioactives with specific functionality. The most well-known among them are lactoferrin and lactoperoxidase, but a variety of cationic proteins and peptides with biodefense properties also belong to this group of micro-components.

It should be appreciated that many of the bioactives known to be present in milk do not function alone but are interactive whereby one activity facilitates or modulates the action of another.

It is anticipated that the cationic fraction may also include small amounts of a number of growth factors; although these growth factors may be present at low levels their action can be potent in stimulating cell repair. These growth factors may include for example: EGF, IGF 1, TGF B1 and TGF B2.

In a preferred embodiment the cationic fraction may also include any other cationic compound of milk. Smolenski et al. (2007) have recently reported on the identity and significant number of minor proteins in bovine milk by Mass Spectrometry (MS) and, in particular, identified a significant number of minor milk proteins that are involved in host defense. Their results are shown in Table 1. This also indicates (in bold) those which may be included in the cationic fraction of the present invention based on their isoelectric points. It should be noted that Smolenski et al. (2007) used SDS-PAGE methods that would not detect low concentration components, such as angiogenin, polymeric immunoglobulin receptor (PIGR) and growth factors.

Table 1. Host defense-related minor proteins identified from milk, showing those that may be extracted as part of the cationic fraction (bold) (reproduced from Smolenski et al., 2007)

TABLE 1

Minor proteins identified in bovine milk.

| ACC Number | Protein Name | Function | pI |
|---|---|---|---|
| NP_777250 | cathelicidin 1 (Bactenecin 1) | antimicrobial properties | 6.8* |
| AAB64304 | chitinase-like protein 1 (CLP-1) | eosinophil chemotactic properties | 8.8 |

TABLE 1-continued

Minor proteins identified in bovine milk.

| ACC Number | Protein Name | Function | pI |
|---|---|---|---|
| Q290092 | endoplasmin precursor (GRP94/GP96) | participates in the assembly of antibody molecules and signalling molecule for polymorphonuclear neutrophils | 4.7 |
| NP_776758 | glucose regulated protein 58 kDa | regulates signalling by interacting with stat3 | unknown |
| NP_776770 | heat shock 70 kDa protein 8 | activated through proinflammatory response mechanisms enhancing MMP-9 expression in monocytic cells | 5.4 |
| NP_071705 | heat shock 70 kDa protein 5 (glucose-regulated protein) | upregulation in macrophages upon IL-4 stimulation | unknown |
| AAA18337 | heat shock protein 27 | inhibitor of neutrophil apoptosis | 5.98* |
| BAA32525 | heat shock protein 70 kDa protein 1A | stress response (refolding and degradation of denatured proteins) | 5.68* |
| AAC98391 | immunoglobulin IgA | antigen recognition | X[1] |
| AAN07166 | immunoglobulin IgD | antigen recognition | X[1] |
| AAB37381 | immunoglobulin IgG | antigen recognition | X[1] |
| AAN60017 | immunoglobulin IgM | antigen recognition | X[1] |
| AAQ88452 | IRTA2 | B-cell immunoglobulin super-family receptor | unknown |
| AAA30617 | lactoferrin | iron binding and antimicrobial peptide "lactoferricin" | 8.67* |
| NP_776358 | lactoperoxidase | oxidative peroxidase activity | 8.327* |
| BAA07085 | lymphocyte cytosolic protein 1 (65K macrophage protein/L-plastin) | regulation of neutrophil integrin function | 5.21* |
| P21758 | macrophage scavenger | mediate the binding, internalization and processing of negatively charged macromolecules | 5.7* |
| AAA36383 | nucleobindin 1 | promotes production of DNA-speicific antibodies | 5.05* |
| NP_776998 | peptidoglycan recognition protein | innate immunity pattern recognition molecule | 9.38* |
| XP_611685 | S100 calcium binding protein A9 (calgranulin B) | associated with S100A8 and implicated in inflammatory response | 6.29* |
| XP_593653 | S100 calcium binding protein A11 (calgizzarin) | upregulation associated with proinflammatory response | 6.7 |
| NP_777076 | S100 calcium binding protein A12 (calgranulin C) | antimicrobial peptide "calcitermin" | 5.9 |
| P42819 | serum amyloid A protein | involved in acute phase cytokine signaling | 6.94 |
| CAA67117 | xanthine dehydrogenase | superoxide anion, hydrogen oxide and peroxxynitrite production | 8.0 |

[1]Immunoglobulins typically have isoelectric points the range of 5.0-9.5. As such, not all bind to the cationic exchange resin.
*The isoelectric points of these proteins have been calculated based on the expected protein structure. (Swiss Prot/TrEMBL, www.expasy.org).

Some of the cationic fraction components (e.g lactoferrin, angiogenin) may also have minor variants,—such as variations in amino acid sequence or in degree and type of glycosylation, these minor variants, and their presence in the cationic fraction should also be taken as being covered by the present application.

According to a second aspect of the present invention there is provided a method of treating or preventing bovine mastitis using a treatment compound substantially as described above, the method characterised by the step of applying the treatment compound onto or into at least one bovine teat.

Throughout this specification the term mastitis should be taken to include both clinical and sub-clinical mastitis. The term mastitis should also be taken to include bacterial, microbial or any other form of mastitis.

It has long been known that at involution (cessation of milking, drying off) there is increased production of the defense proteins which have strong antimicrobial and anti-viral activity, immunomodulatory, and cell growth and repair activities.

During intra-mammary infection or trauma, and involution (cessation of milking, drying off) secretion of the minor defense or regulatory proteins is enhanced (Reiter and Oran, 1967; Schanbacher and Smith, 1975: Talhouk et al., 1996).

The milk lipids (Isaacs et al., 1995) and glycolipids (Newburg, 1996) and sphingolipids (Dillehay et al., 1994: Merrill et al., 1995) also contribute to skin repair and the defense against microbial and viral pathogens. The lipid component of the keratin plug which forms in the teat canal also has antimicrobial properties.

It is well known that lactoferrin, lactoperoxidase, angiogenin, (RNase), N-acetyl glucosaminidase, serum amyloid A, β Defensin and lysozyme are all part of the innate defense system. They play an important part of the natural host defense system against invading micro-organisms, protecting the eyes, the upper respiratory tract, the lactating mammary gland and the intestinal tract of the new born infant.

In a preferred embodiment the cationic fraction extracted from whole milk has the main proteins and growth factors as shown in Tables 2 and 3.

TABLE 2

Sub-fractions from the cationic fraction principal components, as identified by Mass Spectrometry (MS).

| Identity from MS | Total Protein (mg/ml) | % of total | estimated purity (%) |
|---|---|---|---|
| lactoperoxidase[1] | 4.2 | 8.0% | 95% |
| quiescin | 1.6 | 3.0% | 50% |
| jacalin-like protein | 1.4 | 2.7% | 60% |
| chitinase-like protein | 0.4 | 0.8% | 80% |
| angiogenin | 10.0 | 19.0% | 60% |
| lactoferrin | 35.0 | 66.5% | 95% |

TABLE 3

Enzyme-linked Immunsorbent Assay (ELISA) measurement of growth factors in the cationic fraction.

| Fraction | TGFB1 (ng/mg) | TGFB2 (ng/mg) | IGF1 (ng/mg) | IGF2 (ng/mg) |
|---|---|---|---|---|
| angiogenin fraction | 2.0 | 14.5 | 2.2 | 4.7 |
| lactoperoxidase fraction | 7.0 | 109.0 | 4.0 | 5.0 |

From the above tables, the ratios of the three major components, lactoferrin, lactoperoxidase and angiogenin, are 6.2:1.2:1. This is a typical ratio of these main components, but is indicative only.

The innate immune system is the first line of defense against infection, and is up-regulated in response to inflammatory stimuli.

The characteristics of innate immunity include: broad spectrum (non-specific) and lack of memory.

The applicants believe that the cationic fraction of the present invention has a number of modes of action, which act together to form a very effective treatment composition. The cationic fraction has inhibitory (bacteriostatic), bactericidal and immune boosting effects. The synergistic action between sub-components also increases the action of the fraction, in particular in comparison with purified individual sub-components. Similarly, synergistic action between the fraction and the natural immune response can again increase its effectiveness, by opsonising bacterial cells to make them more recognizable by phagoocytes.

It is well known that bovine mastitis (and other forms of mastitis) are a result of infection by a number of differing bacterial species (or other microbial species). It is envisioned that the effectiveness of the present invention to treat mastitis also comes from the action of different sub-components of the fraction acting on different infecting species.

For an in vivo antimicrobial, the basis for antimicrobial action could be said to have two primary mechanisms of potential efficacy:
(1) direct effect of antimicrobial on pathogens, and
(2) immune-boosting activity on the target.

The scientific basis of this hypothesis, however, is as follows. The characteristics of innate immunity in an animal are:
 (i) broad spectrum (non-specific)
 (ii) lack of memory for specific pathogens.

While an enormous number of antimicrobial peptides with diverse sequences have been identified in mammalian systems, a common feature is a cationic amphipathic structure. This structural motif gives rise to a propensity to bind to microbial lipids and disrupt membranes. But that membrane permeabilisation is not always sufficient to cause cell death. However, the synergistic action of a cationic peptide and an agent that acts on the cytoplasm to cause cell death may be bactericidal.

A fraction for milk including a range of the above proteins has previously been extracted and used for the treatment and prevention of periodontal diseases. For example, U.S. Pat. No. 6,544,498 which discloses the extraction by gradient elusion of a basic protein fraction which has an isoelectric point between 7.5 and 11 and a molecular weight distribution of 3,000 to 80,000 Daltons. A broad fraction has also been used for the treatment of osteo problems (U.S. Pat. No. 5,976,597). However, this fraction was limited to 2,000 to 24,000 Dalton, which would eliminate lactoferrin and lactoperoxidase from the fraction. Additionally, this fraction required post-processing to be effective.

Mastitis is very different from periodontal disease, for which U.S. Pat. No. 6,544,498 describes the use of a similar fraction. It would not be obvious to one skilled in the art to use the fraction of U.S. Pat. No. 6,544,498 to treat bovine mastitis due to the significant differences between these conditions:
   Periodontal disease occurs in the mouth, affecting the teeth and gums, where infection occurs on external surfaces. This is a very different environment to the mammary gland which is affected by mastitis on the internal tissue surfaces of the alveoli, ducts and cisterns.
   Periodontal disease leads to loss of alveolar bone. This is irreversible, therefore requiring a preventative or ameliorative treatment. This is again, in direct contrast to mastitis, which leads to reversible tissue damage in the mammary gland, if detected soon enough after onset. For mastitis, preventative or ameliorative treatments are generally not practical, due to the large number of animals to be treated, the manual labor requirements and cost.
   In periodontal disease bacterial entrance and colonization occurs via and within the oral cavity. In contrast, for mastitis cases, bacterial entrance and colonization occurs via the teat canal. In mastitis cases bacterial colonization is aided by a constant rich biological medium—milk.
   U.S. Pat. No. 6,544,498 specifically states in the background art section (paragraph 2) that the conventional treatment using antibacterial mouthwashes has low effectiveness. This indicates that the use of a general antibacterial compound will not be effective. U.S. Pat. No. 6,544,498 argues that the inventiveness of their application is based on the fraction curbing the decrease in alveolar bone and shows experimental data supporting this.
   The disclosure in U.S. Pat. No. 6,544,498 discusses a basic protein fraction which has the main components being lactoperoxidase and lactoferrin. It is disclosed that a daily dose of 1-50 mg per day, of a composition having a fraction content of 0.1-1.0% will be effective at preventing periodontal disease.
   U.S. Pat. No. 6,544,498 however, does not disclose the requirement for detection or diagnosis prior to treatment, that the fraction has any antimicrobial or other action (besides periodontal disease), or the mechanism of action (either direct or immune boosting) and does not teach, mention, discuss or show that there are synergistic effects between the individual sub components, as there are for the cationic fraction of the present invention.

The advantages of the present invention over that in U.S. Pat. No. 6,544,498 include the following:

Treatment of mastitis preferably requires the synergistic effect of all proteins in the fraction, rather than just the three major components.

It is thought by the applicant that treatment of mastitis combines both a direct antimicrobial effect with an immune-boosting effect, including a synergistic effect with the natural immune response.

The cationic fraction of the present invention is extracted from milk from the mammary glands, concentrated and used to treat the same organ (i.e. mammary glands) from which it was extracted. This is highly beneficial as it provides a much more natural treatment. This is not practical for oral applications.

In preferred embodiments the cationic fraction of the present invention may be used on the same animal species from which it is extracted. Again, this provides a more species specific treatment, with components which are not going to be considered 'foreign'. Again, this is not practical with human oral applications.

Daily preventative dosages of the cationic fraction for treating mastitis are not required. Instead, treatment on diagnosis of the condition is utilized.

Despite the industry moving towards more pure forms of milk components, such as lactoferrin for the prevention and treatment of bovine mastitis, the applicant has found that the above components in the innate defense system may not act individually as anti-inflammatory and antimicrobial agents against the range of mastitis producing organisms.

The discovery of the effectiveness of the cationic fraction of the present invention against the micro-organisms which cause or characterize mastitis was made during studies in the advantages in using bioactive fractions extracted on farm versus factory processed milk bioactives. One of the key advantages of bioactives such as lactoferrin (Lf) and lactoperoxidase (Lp), is their anti-microbial activity. Therefore, the applicant set up trials to establish suitable bioassays for characterizing the bioactivities using common pathogens. One of those pathogens was *Streptococcus uberis*.

Interestingly, the applicant found that the inhibitory effects against the pathogen diminished as the cationic bioactive fractions became more purified. This was contrary to common thinking as it is commonly understood that the purer a component is, the more effective it will be.

Considering the origins of these bioactives in cows' milk, the applicant believes they are produced in response to immune challenges within the gland. If there are key biochemical pathways leading to immune success within the mammary gland, there would be synergistic actions between the discrete bioactives, which actually leads to a successful immune response. That is to say, purification of individual parts of the cationic fraction may not be the key to a successful naturally-derived inhibitory product. This led to the hypothesis, which was subsequently tested that the 'total cationic fraction' of the present invention could be used as a successful naturally-derived inhibitory product.

In a preferred embodiment the cationic fraction may be extracted from whole milk.

However, this should not be seen as limiting as the term milk should be taken to include whole milk, skim milk or whey.

It is well known that many conditions affect lactoferrin concentration, such as once or twice daily milking, stress, age, breed, feed types and milking interval. It is anticipated that these factors may also effect the concentration of components within the cationic fraction, or the fraction itself.

It is also well known that many milk components are increased in colostrum. Although the cationic fraction of the present invention may be extracted from colostrums it is anticipated that this will not be the main source for the following reasons: firstly there is only a short period of time when colostrum is produced, and secondly colostrum is more difficult to process through most extraction media, for example cation exchange media.

It should be appreciated that the term milk may include any raw (or unprocessed) milk. This is taken to include raw milk which has been chilled, incubated, or stored, at either a chilled or ambient temperature.

Throughout this specification the term 'milk derived substance' should be taken as meaning any pre-processed milk, i.e. not raw (or unprocessed) milk. It should be appreciated that processing may include a number of standard or unique processing procedures such as centrifugation, pasteurisation, acidification, or any other standard dairy factory or processing techniques.

The term 'milk derived substance' should also be taken to include any post-processing techniques. For example, freeze-drying, solid product forms and liquid product forms.

In one preferred embodiment the cationic fraction may be extracted from bovine milk.

However, this should not be seen as limiting, as the cationic fraction may also be extracted from other mammalian species, including, but not limited to sheep, goats, buffalo, camels and humans.

In one embodiment the proportions of the different cationic components within the cationic fraction may be as extracted, or concentrated.

However, this should not be seen as limiting, as it may be desirable to alter or control the ratio of at least one, or a number of components respectively. It should be appreciated that any such alteration in the proportions of the cationic fraction components are covered by this disclosure.

In one preferred embodiment the cationic fraction may be extracted "on-farm", during or directly after the milking process. This may be advantageous as some of the components may be lost, damaged or denatured during subsequent handling, storage, fat removal, or other processing steps.

However, this should not be seen as limiting as the cationic fraction of the present invention may also be extracted once the milk has been collected on farm, or after the milk has left the farm during any further storage, transport or processing step.

In the case of the cationic fraction being extracted from milk that is processed in the usual manner involving storage, transport and conversion to skim milk or whey the temperature should preferably be maintained at substantially 4-7° C. to minimize microbial growth.

In the case of the cationic fraction being extracted from whole milk the temperature should preferably be maintained at not less than 35 C to ensure that lipids remain in a liquid state so that they can easily pass through the extraction material. And to ensure the bioactivity of the factors in the cationic fraction are maintained at or close to the endogenous state.

In an alternative embodiment the cationic fraction may be extracted from genetically modified animals, for example genetically modified enhancement of lactoferrin production in dairy cows. One skilled in the art would realise that extraction from the milk of genetically modified animals may affect the ratio or concentrations of lactoferrin, or other components in the cationic fraction, or a whole cascade of key components.

In one preferred embodiment the cationic fraction may be extracted from the same species of animal that the treatment substance is intended to be used on. For example a cationic fraction extracted from cow milk to treat/prevent bovine mastitis, or a cationic fraction extracted from goat milk to treat mastitis in goats.

In a preferred embodiment the final product or cationic fraction may be used for the treatment or prevention of bovine mastitis.

One major advantage of the use of the cationic fraction of the present invention in the prevention or treatment of bovine mastitis is that it is from milk and is therefore considered to be natural and safe to use.

The cationic fraction of the present invention does not have a withholding period as antibiotics, or many other treatments do, and cannot contaminate the milk, as antibiotics can, for example when the cow has been treated and recovered from mastitis but may still have traces of antibiotics in the milk.

In a preferred embodiment the cationic fraction may be used to form part of a final treatment composition, and shall be referred to as such herein. However this should not be seen as limiting as in some instances the cationic fraction alone may be administered for the prevention and treatment of bovine mastitis.

The final composition may also include other compounds which may include antibiotics and analgesics.

For use in a milking cow the cationic fraction may preferably be incorporated with an aqueous solution, such as a buffer. This more dilute form could be prepared from a concentrate, which was made from a concentration step, for example, by ultrafiltration.

In one preferred embodiment the final treatment composition may be in the form of a liquid.

This may include for example: teat sprays, teat wipes, udder/teat washes, milking cluster backflush solutions or intramammary formulations for either lactating or non-lactating animals.

Liquid treatments for use in a milking cow may be massaged or applied up into the udder after milking.

However this should not be seen as limiting, as the final treatment composition could also be in the form of an oil, an emulsion, a powder, a gel or cream or as a solid putty like material.

In an alternative embodiment the final composition may be in the form of a teat seal. One skilled in the art would realize that the teat seal formulation may be in a range of configurations, for example, it may solidify after application, or may in a more solid form. The teat seal type of treatment is typically applied near or within the teat canal entrance.

Currently, it is anticipated that the dosage regime of the composition of the present invention may be within the range of 1 g/day in a 10 ml dose once a day for three days. This relates to 1 g of total protein, made up to the 10 ml dose in a pharmaceutically acceptable carrier or buffer, for example Ringer's salts.

Throughout this specification the term final treatment composition should be taken as meaning the form in which the cationic fraction is administered to the animal.

The final treatment composition may include at least one or more of the following: carriers, buffers, preservatives, excipients or other pharmaceutically acceptable components required to ensure the cationic fraction is in a form that is easily dispensed, used and is efficient for the purpose of preventing and treating mastitis.

In one embodiment the final treatment composition may also include at least one component which is capable of controlling the time release of the composition. This may be used to effectively treat mastitis over an extended period of time. Known components which could be used for this purpose would be well known to one skilled in the art.

In a preferred embodiment the cationic fraction may be provided in the final treatment composition in a concentration range of 2-20% (w/w). This concentration is believed to provide the greatest ease in application with respect to the volume being injected into the teat. It should be appreciated that this may differ substantially based on the application method or volume being used.

In a preferred embodiment the cationic fraction may be mixed with an inert liquid carrier.

In the embodiment where the final treatment composition is for use as a teat seal the final composition may also incorporate any 'hardening' component added to block the teat canal and physically prevent microbes from entering same. In some instances the final treatment composition configured for use as a teat seal may become substantially more solid when placed in the teat canal, thereby also physically preventing the entry of micro organisms.

In a preferred embodiment the cationic fraction of the present invention may be used to treat cows during the drying off or dry period.

In an alternative embodiment the cationic fraction may be utilized during the milking or lactation period. In this instance it is preferable that the cationic fraction, or final product containing the fraction is in a liquid form as it is undesirable to block teats during the milking period.

According to another aspect of the present invention there is provided a treatment formulation which includes, a treatment composition extracted from milk, or a milk derived substance, wherein the fraction contains at least two components with an isoelectric point of or greater than substantially 6.8, and a cell lysing substance.

In a preferred embodiment the treatment formulation may be an antimicrobial.

In a preferred embodiment the treatment formulation may also include one or more of the following:

1. a peroxidase substrate, and/or
2. hydrogen peroxide or a source of hydrogen peroxide.

In a preferred embodiment the treatment substance may be the cationic fraction substantially as previously described. This included lactoferrin, lactoperoxidase and angiogenin as its main components.

In a preferred embodiment the cell-lysing substance may be any compatible compound, or combination of compounds that are capable of fully, or partially lysing the cell wall.

In one embodiment the cell lysing substance may be a detergent-like substance.

In one preferred embodiment the cell lysing substance may be a monoglyceride.

In one preferred embodiment the monoglyceride may be monolauryl glycerol.

Monolauryl glycerol is a monoglyceride consisting of lauric acid covalently bonded to a glycerol molecule through an ester linkage. Lauric acid is believed to have the highest cell lysing action of any of the fatty acids which could potentially be incorporated into the monoglyceride.

However, it should be appreciated that any other monoglyceride—i.e. with a different fatty acid chain may also be utilized, as long as this has some cell lysing action In a preferred embodiment the peroxidase substrate may be any substrate or compound on which lactoperoxidase or any other peroxidase enzymes may act.

In one preferred embodiment the peroxidase substrate may be thiocyanate.

In one particular preferred embodiment the peroxidase substrate may be potassium or sodium thiocyanate. Alternatively any other thiocyanate which can act as a peroxidase substrate may be utilized.

In a preferred embodiment the minimum concentration of peroxidase substrate is 20 ppm (when the peroxidase substrate is sodium thiocyanate), 20 ppm (when the source of hydrogen peroxide is ascorbate) and 5 ppm (when the cell lysing agent is monolauryl glycerol) (as shown in vitro).

However, one skilled in the art would realize that these may differ depending on the type of composition being applied, i.e. a liquid or a paste and the specific site of application or action.

One skilled in the art would also realize that in vivo, the site of application may already have peroxidase substrate present. In this case it may not be required to be included in the formulation, or may be able to be included at a lower concentration.

In a preferred embodiment the source of hydrogen peroxide used may be ascorbate or ascorbic acid.

Ascorbate and ascorbic acid have been shown in previous publications to be good substrates for peroxidase enzymes. This is a preferred source of hydrogen peroxide as it is stable—unlike peroxide itself.

Hydrogen peroxide is also a substrate of peroxidase enzymes. Therefore, one skilled in the art would realize that the same considerations would apply as discussed above in relation to the peroxidase substrate.

Substrate (in the form of hydrogen peroxide or another substrate) is preferably included for lactoperoxidase only. Lactoperoxidase is the only one of the major components of the cationic fraction which is an enzyme. A substrate is required for lactoperoxidase (unless already present) in order to convert thiocyanate to a biocidal compound.

It will be appreciated that the cationic fraction may contain other enzymes, and that substrate for same may be incorporated into the composition to increase efficiency.

In a preferred embodiment the formulation containing additives may be used for dairy purposes as discussed above in relation to the cationic fraction alone.

However, this should not be seen as limiting as the formulation containing additives has a general antimicrobial action, and could be used for a wide number of additional applications. These include for example: soaps, cleaning agents, food-grade coatings, wound/ulcer/cold sore dressings or topical treatments to name a few. One skilled in the art would readily realize that the formulation with additives could be used in any application where a general antimicrobial agent is required.

The applicant has found, as shown in the best modes method section that, in vitro, the cationic fraction with the addition of thiocyanate and ascorbate (i.e. a peroxidase substrate and a source of hydrogen peroxide) has significantly greater action against a range of bacterial species than the isolated individual components of the fraction.

According to another aspect of the present invention there is provided a method of extracting a treatment compound substantially as described above from milk, including the steps of:

a) passing milk through an extraction material, and
b) eluting a fraction of the bound milk components
   wherein parameters of the extraction process provides a cationic fraction which includes at least lactoferrin, lactoperoxidase and angiogenin,
the method characterised in that the step b) is conducted once.

In a preferred embodiment the extraction material may be a cation exchange material. This may either be in the form of resin, expanded bed resin, magnetic beads, membrane or other suitable form for large scale extraction.

In a preferred embodiment the cation exchange material may be any material that has sufficient mechanical strength to resist high pressures and maintain high flow rates.

In a preferred embodiment the cation exchange resin may have a mean particle size in excess of 100 µm. Resins in larger bead form have been developed for use with viscous feed streams because they do not pack as closely as smaller beads therefore there are wider channels so that there is not excessive back-pressure.

Examples of suitable cation exchange resins are SP-Sepharose Big Beads, SP-Sepharose Fast Flow, SP-Toyopearl and S-Ceramic HyperD.

One example of an extraction and purification process is as follows:

Lactoferrin binds firmly to cation exchange and is the last major protein to elute in a salt gradient. Therefore a single step elution with 1M salt (80 mS-100 mS) elutes all proteins and peptides in a single fraction (cationic fraction). Elution with 80-100 mS salt following a prior 40 mS elution will yield a fraction that is primarily lactoferrin.

After lactoferrin, lactoperoxidase is the next most abundant of the cationic proteins captured by ion exchange from milk (0.03-0.075 mg/ml milk). In a salt gradient lactoperoxidase elutes from cation exchange before lactoferrin at 25-30 mS.

The growth factors EGF, IGF 1, IGF 2, TGF B1 and TGF B2 are present in milk in ng/ml quantities, and have been shown to be captured by cation exchange.

A number of other biologically active cationic peptides elute between lactoperoxidase and lactoferrin at 35-40 mS (intermediate fraction). Therefore the concentration of salt used at each step in the elution determines whether these biologically active peptides are in the lactoperoxidase fraction or the lactoferrin fraction.

Immunoglobulins are eluted in low salt (15-20 mS).

In a preferred embodiment the milk, or milk product may be passed through a membrane having cationic exchange properties, or a column packed with the cationic exchange resin or a batch reactor with suspended cationic resin, whereby the micro-components adsorb from the starting milk or product thereof onto the cationic exchange resin or membrane.

After adsorption of milk micro-components the cationic fraction is preferably extracted by elution with a salt solution.

However, this should not be seen as limiting as elution of the cationic fraction may also be via a shift in pH. This method, however, is not popular in large scale commercial processes as the high pH required to remove lactoferrin from the resin could be damaging to the lactoferrin, or in the present case any other components in the cationic fraction.

In a preferred embodiment, before elution, the resin or membrane may be rinsed with a salt solution. Preferably the rinse solution may be sodium chloride or sodium bicarbonate, with conductivity between 5 and 10 mS (millisiemens/ cm). This rinse step ensures that substantially all non-adsorbed milk components are rinsed off the resin or out of the membrane.

In a preferred embodiment the cationic fraction may be eluted in a salt gradient between substantially 10 mS and 100 mS conductivity (0.1 to 2.0 M salt).

In a preferred embodiment the cationic fraction may be eluted in a single fraction by passing a salt solution with conductivity between 80 and 100 mS through the column or membrane.

In a preferred embodiment the elution salt may preferably be sodium chloride. However, this should not be seen as limiting as other salts including sodium acetate, sodium bicarbonate, ammonium bicarbonate, or potassium chloride may be used.

Having the cationic fraction eluted in a one-step elution provides a significant advantage. It decreases the length of extraction time thereby decreasing the possibility of bioactives being denatured. It also decreases the time, labour and cost of the extraction process. This can provide a significant advantage, especially on a large scale.

In a preferred embodiment after initial monitoring of the protein levels in the eluted stream to determine the concentration of salt and the volumes required to elute all the protein, the typical large scale process operates on volumes rather than continuous monitoring.

In a preferred embodiment the extraction may be undertaken in a continuous manner.

In another preferred embodiment, the extraction may be undertaken in a batch elution.

In the above preferred embodiments the cationic fraction may be extracted by a 'one-step' process, by step elution.

In an alternative embodiment the cationic fraction may be extracted using a gradient elution.

However this should not be seen as limiting as the cationic fraction may also be extracted in independent fractions and recombined to form the complete cationic fraction at a later stage.

In some embodiments the cationic fraction may undergo further treatments, by standard techniques known in the art, for example, to remove salt, or to concentrate, or to filter for sterility or to remove endotoxin. The concentrated fraction may also be lyophilised.

In a preferred embodiment the cationic fraction may be concentrated to approximately 20% solids.

The present invention has a number of significant advantages over prior methods of preventing and/or treating bovine mastitis, these include the following:

Having the cationic fraction eluted in a one-step elution decreases the length of extraction time required for extraction, thereby decreasing the possibility of bioactives being denatured. It also decreases the time, labour and cost of the extraction process. This can provide a significant advantage, especially on a large scale.

The cationic fraction of the present invention is from milk and is therefore considered to be natural and safe to use.

The cationic fraction of the present invention does not have a withholding period as antibiotics, or many other treatments do, and cannot contaminate the milk or meat, as antibiotics can, for example when the cow has been treated and recovered from mastitis but may still have traces of antibiotics in the milk or meat.

It is more effective for the prevention and treatment of bovine mastitis than each individual component alone.

Provides a non-antibiotic treatment option for organic farmers.

Provides a non-antibiotic treatment for those concerned that the wide-spread use of antibiotics in animal treatments is contributing to an increase in the incidence of antibiotic resistance in bacteria.

Mastitis occurs in the mammary gland which is a unique and specific environment. Mastitis is caused by a wide range of pathogens making it difficult to treat with a single compound. The formulation overcomes this problem and is active against a number of mastitis (and other) pathogenic species.

The formulation of the present invention can be extracted from the organ and species on which it is to be used—making it more specific.

It can be administered once mastitis has been diagnosed.

Provides a synergistic effect between a number of components within the cationic fraction—again including efficiency and activity.

Provide a direct antimicrobial and anti-inflammatory effect as well as an immune boosting effect.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

Figure 1:
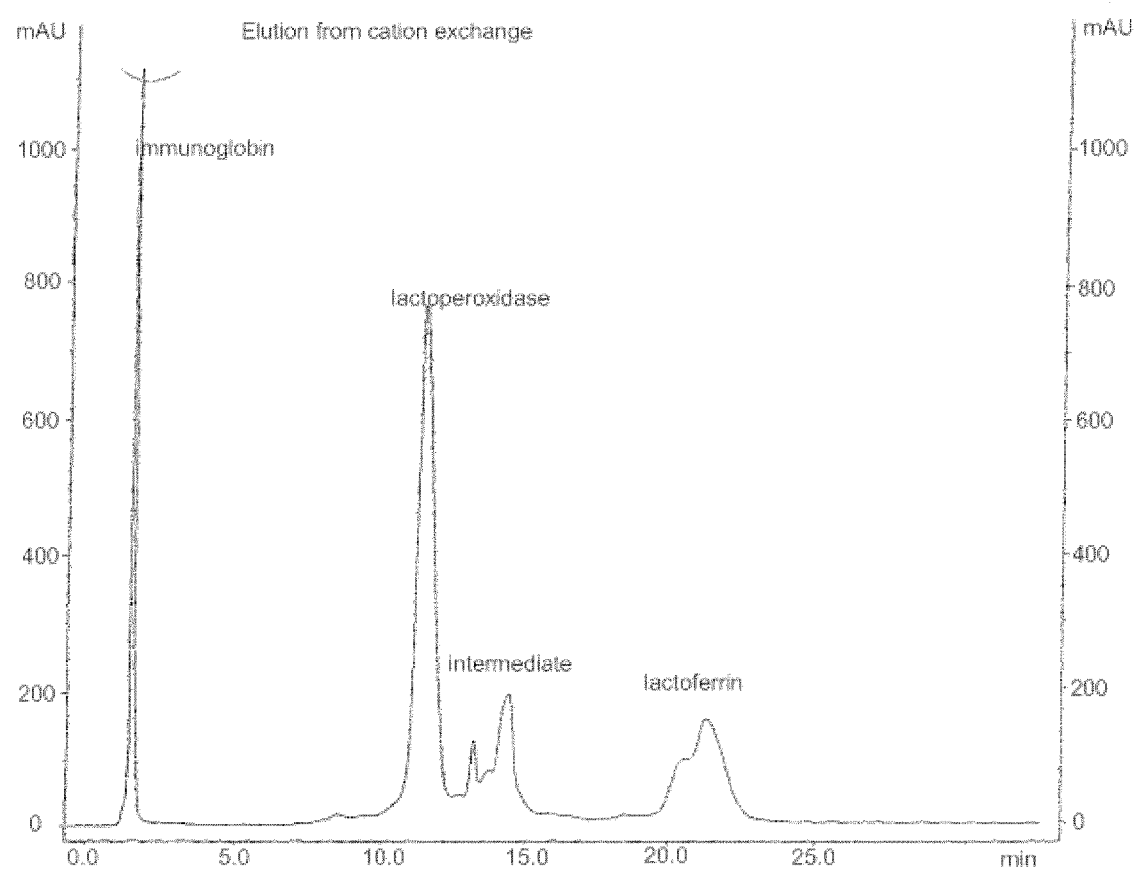
FIG. 1 shows the general elution profile of all the fractions from cation exchange

FIG. 1 shows the elution profile of the cationic fraction from cation exchange. This represents all the protein peaks (as detected at 280 nm) that would be present in a single fraction eluted in a gradient from 80-100 mS. The main components in the cationic fraction are immunoglogulin, lactoperoxidase, lactoferrin, and a group of minor components that include angiogenin.

Figure 2:
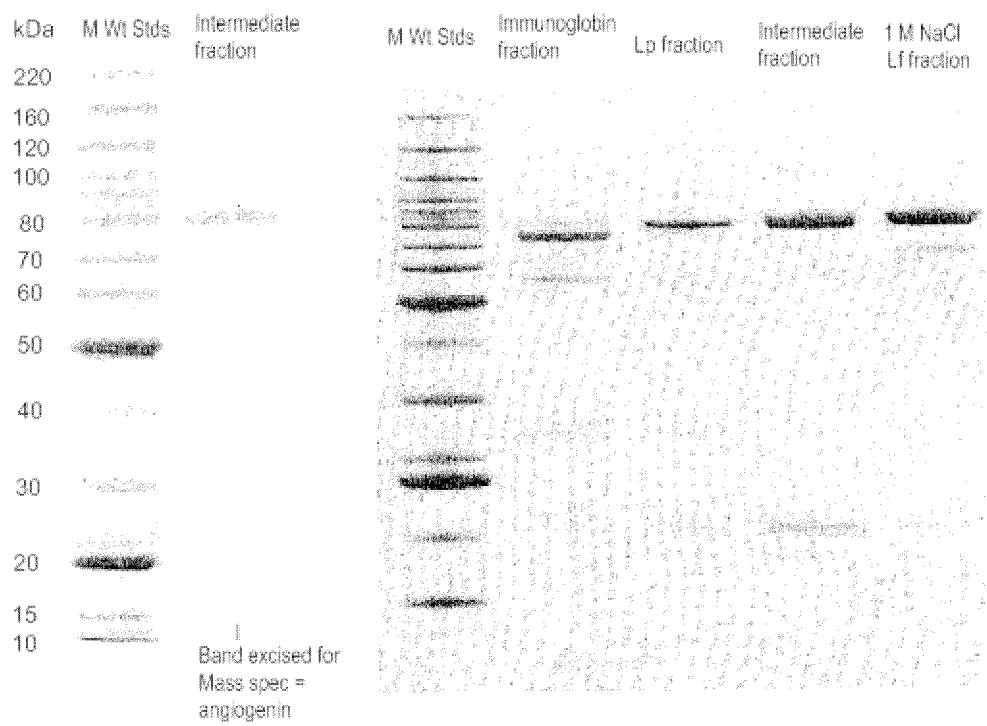
FIG. 2 shows the fractions separated on SDS_PAGE, and indicates the band that was excised for Mass Spectroscopy and identified as bovine angiogenin.

FIG. 2 shows the main fractions separated on SDS-PAGE, and indicates the band that was excised for Mass Spectroscopy and identified as bovine angiogenin.

The immunoglobulin fraction shows PIGR (76 kDa) as the predominant band, and the heavy (52 kDa) and light chains of immunoglobulin.

The Lp fraction is mainly lactoperoxidase with a small amounts of heavy and light chains of immunoglobulin and angiogenin.

The intermediate fraction has a prominent band of lactoferrin and lactoperoxidase (80 kDa) and a band at around 15 kDa that was identified by Mass Spectrometry as angiogenin, a band at approximately 13 kDa that was identified by Mass Spectrometry as jacalin-like.

The Lf fraction is predominantly lactoferrin (80 kDa).

Experimentation Undertaken:

To test the hypothesis that the cationic fraction could be used as a successful naturally-derived inhibitory product, a variety of in vitro experiments have been conducted on the inhibitory effect of the cationic fractions captured from milk by cation exchange. These experiments have been summarized into several areas.

1. Radial Diffusion (RD) agar assays
2. Minimum Inhibitory Concentration (MIC) assays in microtitre plates The applicant has also tested various cationic sub-fractions versus the total cationic fraction to determine inhibition efficacy against the three most common major mastitis-causing pathogens: *Streptococcus uberis*, *Staphylococcus aureus* and *Escherichia coli*.

The applicants have also aimed to form a formulation that is effective against all three pathogens. Since the activity of the fraction was lower against certain pathogens, the applicant has also explored various additives to the formulation to achieve this 'one formulation' goal.

1. Extraction of the Cation Fraction

The process of producing the cationic fraction involved fractionating milk through a cation exchange resin, eluting the bound components from the resin using a salt solution, which can be either a one-step high molarity (>1M) salt or a gradient elution from a lower molarity up to over 1M, collecting the eluted components in a single fraction, and then desalting and purifying the collected fraction.

The cationic fraction was analysed for its constituent components, and the results shown in Tables 2 and 3 (reproduced below). Table 2 shows a typical result for yield and identity of the major proteins identified in the cationic protein fraction.

This particular cationic fraction was captured from raw, whole milk. Growth factors, TGFB 1, TGFB 2, IGF1 and IGF2 are present in low amounts, and are detectable by ELISA in freeze dried concentrates (Table 3).

TABLE 2

Sub-fractions from the cationic fraction, as measured by Mass Spectrometry (MS). ([1]Lactoperoxidase was determined via extinction coefficient rather than MS.)

| Identity from MS | Total Protein (mg/ml) | % of total | estimated purity (%) |
| --- | --- | --- | --- |
| lactoperoxidase[1] | 4.2 | 8.0% | 95% |
| quiescin | 1.6 | 3.0% | 50% |
| jacalin-like protein | 1.4 | 2.7% | 60% |
| chitinase-like protein | 0.4 | 0.8% | 80% |
| angiogenin | 10.0 | 19.0% | 60% |
| lactoferrin | 35.0 | 66.5% | 95% |

TABLE 3

Enzyme-linked Immunsorbent Assay (ELISA) measurement of growth factors in the cationic fraction

| Fraction | TGFB1 (ng/mg) | TGFB2 (ng/mg) | IGF1 (ng/mg) | IGF2 (ng/mg) |
| --- | --- | --- | --- | --- |
| angiogenin fraction | 2.0 | 14.5 | 2.2 | 4.7 |
| lactoperoxidase fraction | 7.0 | 109.0 | 4.0 | 5.0 |

2 Radial Diffusion Assay

Methodology

Growth medium (appropriate for the selected organism) was inoculated with a fresh culture of the organism and poured in a thin layer into a petri dish.

When the agar set, wells were cut (with a sterile cork borer), the agar plug was removed, and each well was filled with a test sample.

The petri dishes were incubated overnight (at the temperature appropriate for the organism).

If the test sample has inhibited the growth of the organism, clear zones with no growth were observed around the wells.

Results Summary

Figure 3:
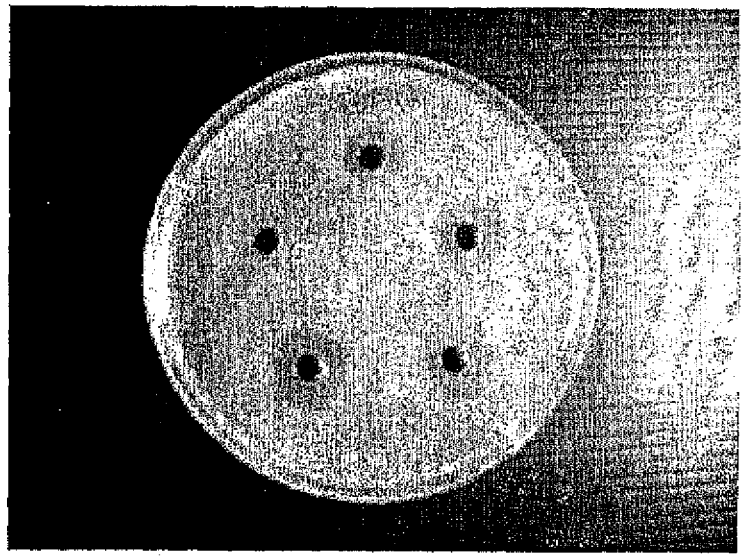
FIG. 3 shows a radial diffusion assay plate, for *Streptococcus uberis*.

FIG. 3 shows a radial diffusion assay plate for *Streptococcus uberis*. In this experiment, the goal was to test various additives into the formulation, isolating the additives' effect from the cationic fraction's effects. On this plate, the sources were (1) whole cationic fraction (20-40 mg/ml) with sodium thiocyanate (500 ppm) and monoglyceride (250 ppm) and (2) sodium thiocyanate (500 ppm) and monoglyceride (250 ppm) alone. The total formulation is shown in four spots starting clockwise from the '12 o'clock' position. The additives alone spot is in the o'clock position. Consistently large and clear zones for the total formulation can be seen, while no inhibition from the additives alone was observed.

Figure 4:
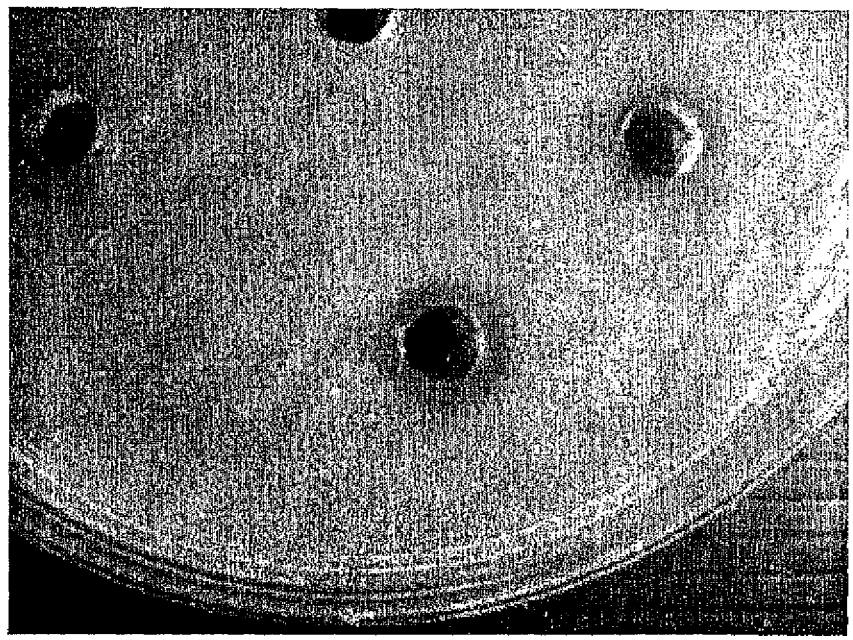
FIG. 4 shows a radial diffusion assay plate, for *Staphylococcus aureus*.

FIG. 4 shows a radial diffusion assay plate tested against *Staphylococcus aureus*. In this experiment, various combinations of the cationic fraction with and without the additives, sodium thiocyanate (500 ppm) and monoglyceride (250 ppm), were used. While the inhibitory effects were less than those against *Streptococcus uberis*, one can see that the cationic fraction alone (3 o'clock position) and the total formulation (6 o'clock position) resulted in inhibitory zones. The additives alone (12 o'clock position) and the cationic fraction with sodium thiocyanate (9 o'clock position) achieved no inhibition, suggesting that the monoglyceride is a key component for the formulation against *Staphylococcus aureus*.

3 Minimum Inhibitory Concentration (MIC) Assays

Assays in microtitre plates, while more time consuming, allow a greater range of dilutions of sample and additives to be tested. Also samples can be taken from the wells with no growth to determine whether the organisms have been killed or merely inhibited.

Methodology

Dilutions of the test sample plus various additives were placed in the wells of a microtitre plate.

A small inoculum of the bacterial culture was added to each well.

The plate was incubated at the appropriate temperature.

A spectrophotometric microtitre plate reader was used to measure the turbidity (absorbance at 450 nm) in each of 96 wells every 30 minutes for 18 hours.

Results Summary

Figure 5:
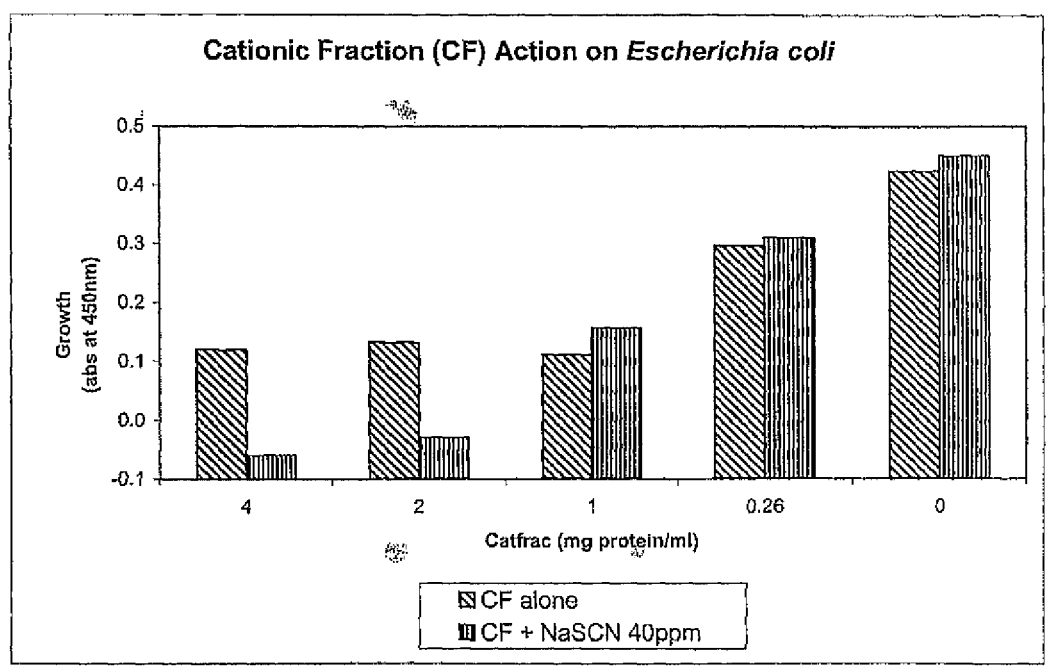
FIG. 5 shows a graph of *Escherichia coli* inhibition using the cationic fraction alone, and with 40 ppm of sodium thiocyanate.

In graphical form, FIG. 5 shows the extent of growth of the *Escherichia coli* indicated by the height of the bars. The shortest bars show maximum inhibition of growth. For this figure, the left-hand bars indicate that some inhibition of growth is achieved with the cationic fraction alone at a concentration of 1 mg/ml. However, adding 40 ppm of sodium thiocyanate to the cationic fraction allowed total growth inhibition to occur at a cationic fraction concentration of 2 mg/ml. This indicates that lactoperoxidase contributes to the antimicrobial activity when its substrate (thiocyanate) is included.

Figure 6:
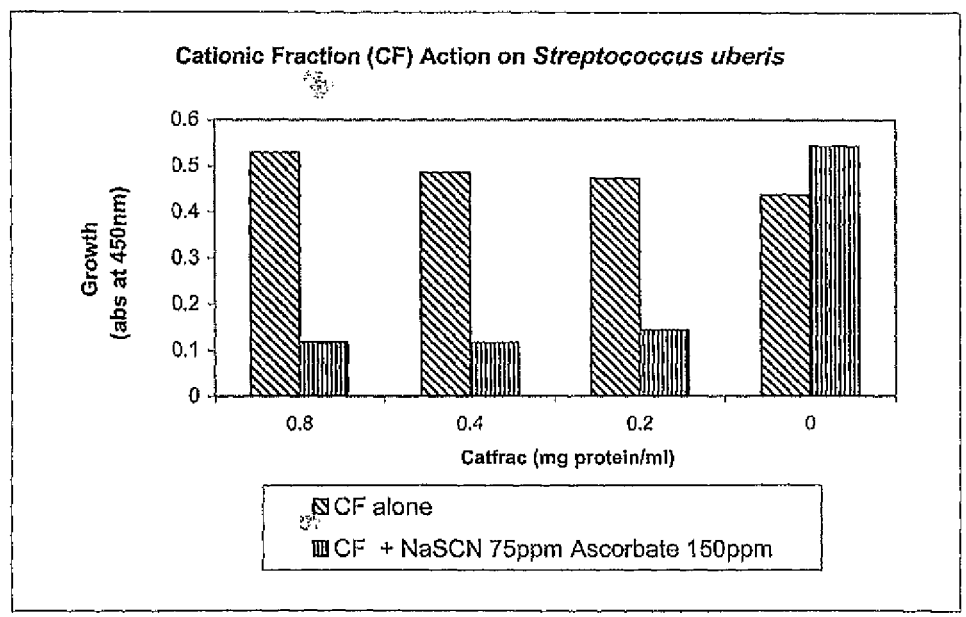
FIG. 6 shows a graph of *Streptococcus uberis* inhibition using the cationic fraction alone, and with 75 ppm of sodium thiocyanate and 150 ppm of ascorbate.

FIG. 6 shows the results of a different formulation of the cationic fraction against *Streptococcus uberis*, this time using sodium thiocyanate (75 ppm) and ascorbate (150 ppm). Against *Streptococcus uberis*, there is no inhibition in vitro using the cationic fraction alone up to 0.8 mg/ml. However, adding sodium thiocyanate and ascorbate shows an inhibitory effect occurring as low as 0.2 mg/ml of the cationic fraction. This confirms that in the absence of milk (or another natural source of substrates) the addition of thiocyanate (as substrate) and ascorbate (as a source of peroxide) is essential for inhibition of *Streptococcus uberis*.

Note that in FIG. 6, none of the additives were totally inhibitory on their own. The samples labeled '0' in the figure are buffer-only and additive-only samples.

In order to determine conclusively that the total cationic fraction is at work in a synergistic way, MIC experiments were set up using *Staphylococcus aureus* as the pathogens. A target formulation of sodium thiocyanate (20 ppm) and ascorbate (20 ppm) was chosen from past experimental work. The cationic fraction was fractionated by size-exclusion chromatography into six (6) individual sub-fractions, each containing a major bioactive protein constituent of the total cationic fraction. Each of these six (6) individual fractions was then recombined to form a seventh treatment. Finally, an unfractionated cationic fraction was tested as an eighth treatment. Concentrations of each cationic fraction were chosen such that each sub-fraction protein content from Table 2 was adjusted so that it was equivalent to its concentration in the recombined sample.

Figure 7:
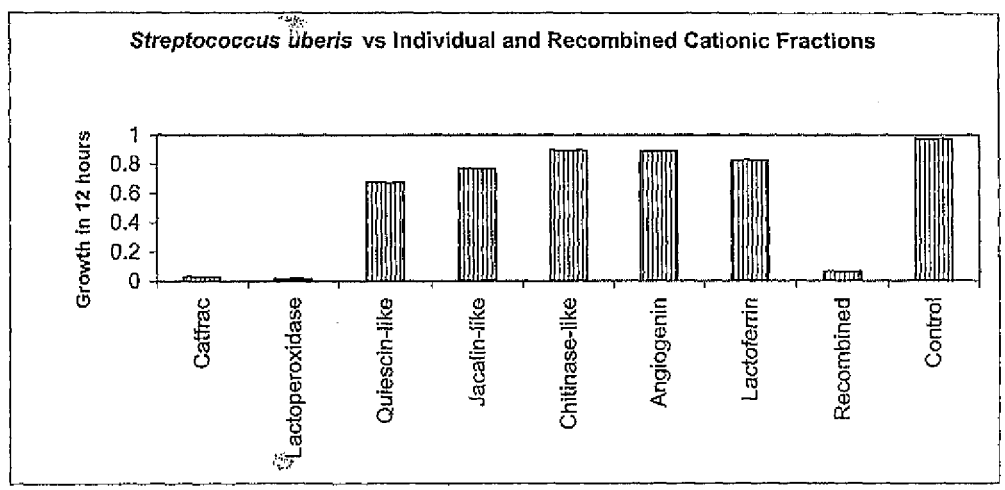
FIG. 7 shows a graph of *Streptococcus uberis* growth using various ub-fractions of the cationic fraction, a recombined cationic fraction and an unfractionated (whole) cationic fraction.
Figure 8:
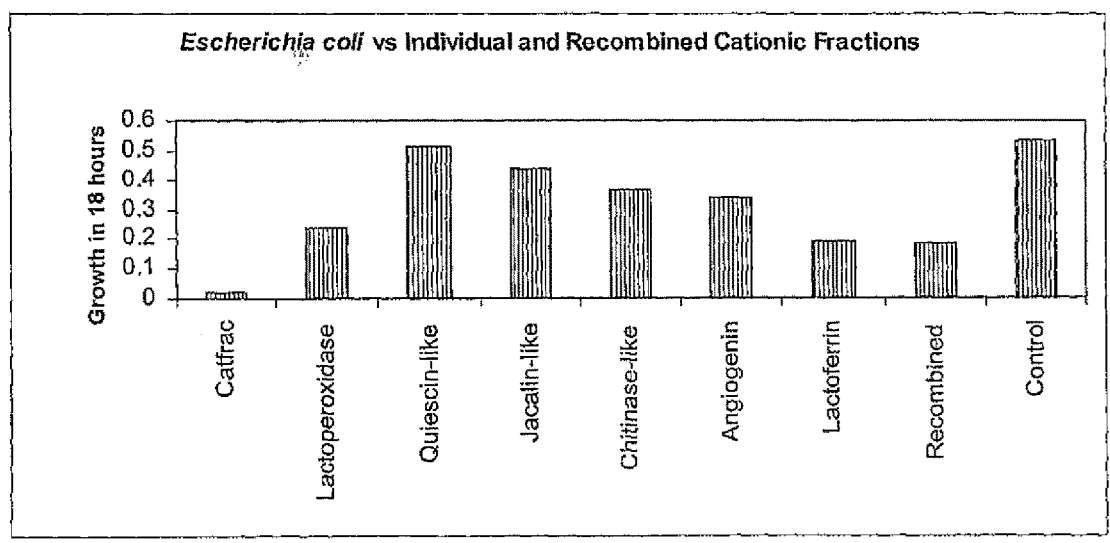
FIG. 8 shows a graph of *Escherichia coli* growth using various sub-fractions of the cationic fraction, a recombined cationic fraction and an unfractionated (whole) cationic fraction.
Figure 9:
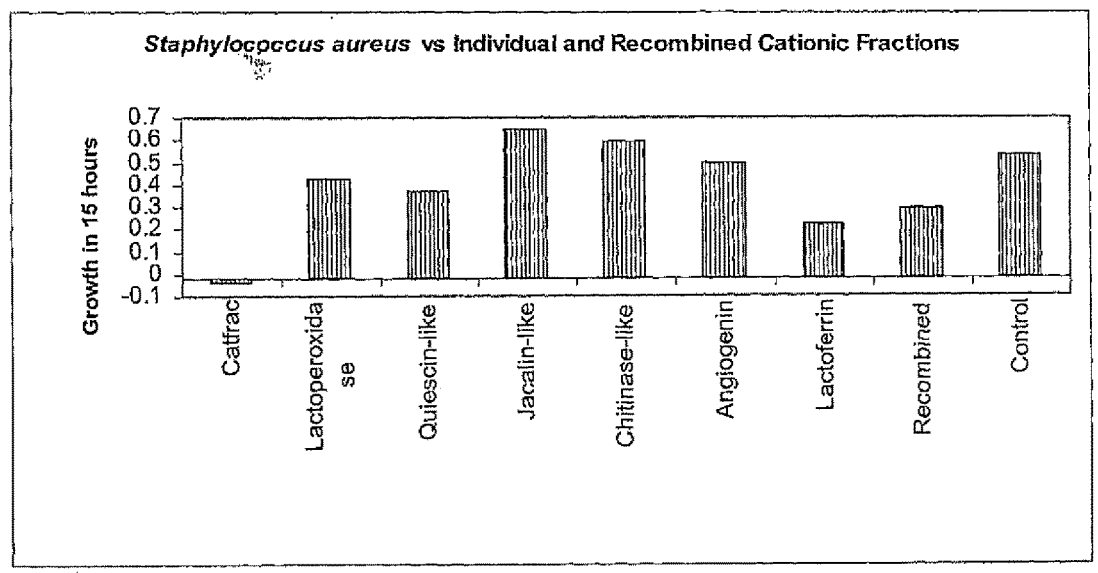
FIG. 9 shows a graph of *Staphylococcus aureus* growth using various sub-fractions of the cationic fraction, a recombined cationic fraction and an unfractionated (whole) cationic fraction.

FIG. 7 shows the growth of *Streptococcus uberis* after 12 hr for each sample. Note that for this pathogen, the Lp fraction itself shows as much inhibition as the total cationic fraction. FIG. 8 shows the growth of *Escherichia coli* after 18 hr for each sample. For this pathogen, the total cationic fraction is required to achieve maximum inhibition. This is also the case for *Staphylococcus aureus* (FIG. 9). The conclusion from these experiments is that, in order to achieve a target formulation active against all three major mastitis pathogens, the total cationic fraction is required. Recombining individual sub-fractions could be used, however, a total eluted fraction would be preferred.

At this stage, there is strong evidence that a total cationic fraction from the milk inhibits the growth of all three of the most common mastitis pathogens to varying degrees. While pathogen-specific formulations could be made, we also believe that a formulation can be achieved that can be commonly used against all three pathogens.

4. Test of Growth in Full Cream Milk and Nutrient Media

Figure 10:
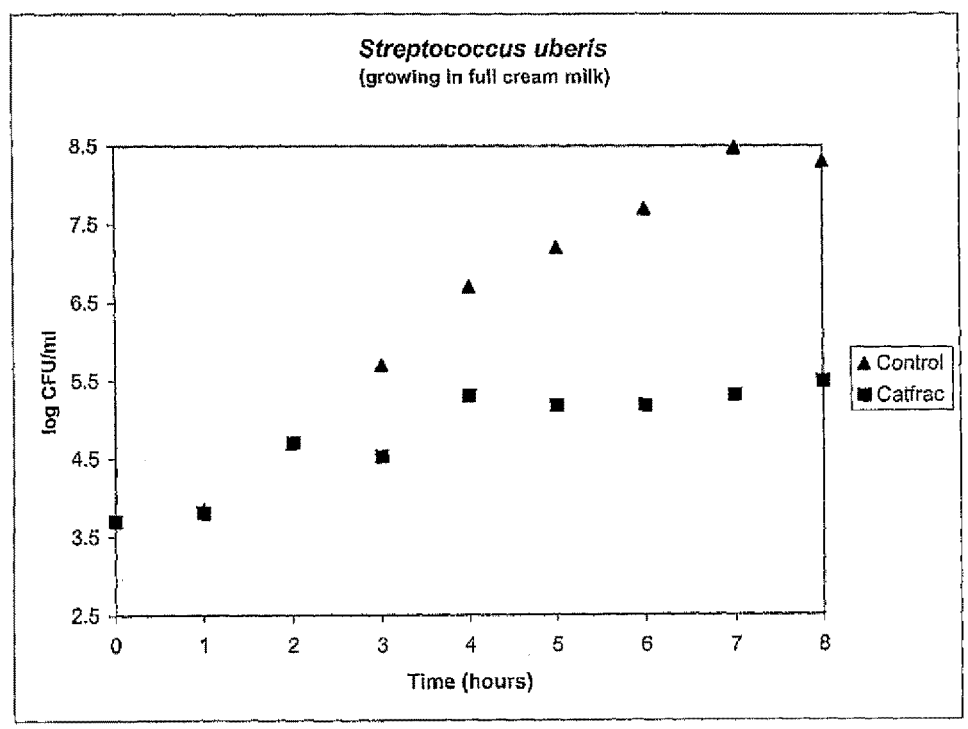
FIG. 10 shows a graph of the effect of the cationic fraction on the growth of *Streptococcus uberis* in full cream milk.

The effect of the cationic fraction on the growth of *Streptococcus uberis* in full cream milk was tested, with results shown in FIG. 10.

At time zero autoclaved milk was inoculated with 0.1 ml of *Streptococcus uberis* (1/1000 dilution of logarithmic phase growth in trypticase soy broth). After two hours cationic fraction at a final concentration of 5 mg protein/ml was added to two flasks and two were kept as controls. Samples were removed for plate counts at hourly intervals. The growth curves (average of the plate counts) are shown in FIG. 10. The addition of the cationic fraction has inhibited the growth of *Streptococcus uberis* while the control has reached maximum growth in 7 hours. This experiment shows that there was no requirement for the addition of thiocyanate or ascorbate when *Streptococcus uberis* was grown in milk.

Figure 11:
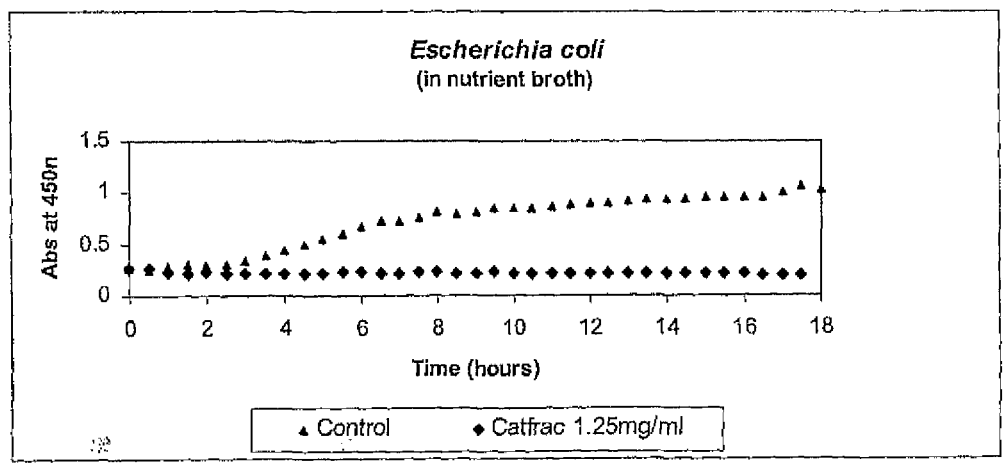
FIG. 11 shows a graph of the effect of the cationic fraction on the growth of *Escherichia coli* in nutrient media in a microtitre plate.
Figure 12:
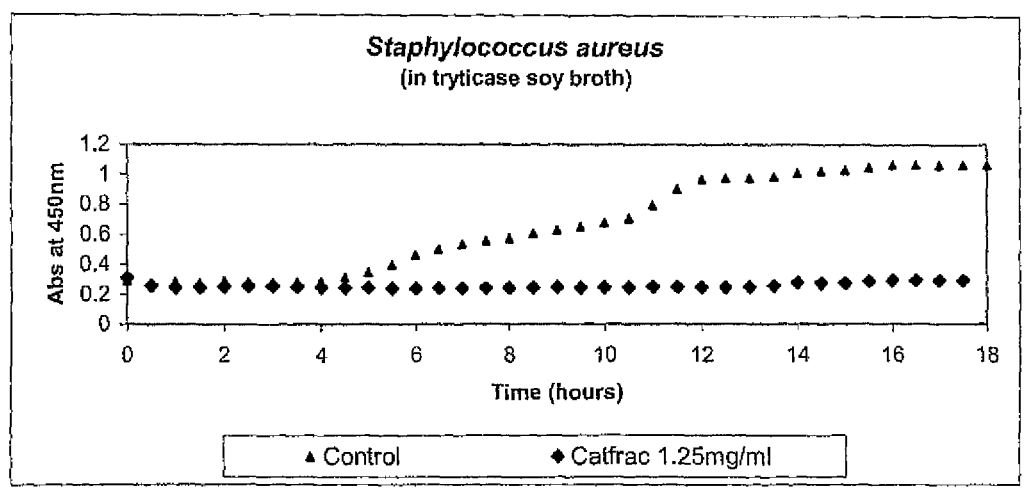
FIG. 12 shows a graph of the effect of the cationic fraction on the growth of *Staphylococcus aureus* in nutrient media in a microtitre plate.

The effect of the cationic fraction on the growth of *Escherichia coli* and *Staphylococcus aureus* is shown in FIGS. 11 and 12.

5. Efficacy Trial

The applicant is undertaking efficacy trials in the next six months.

The basis for this trial is as follows:

Aims: determine efficiency of treatment, and whether there are any toxicity issues with either the cationic fraction or additives/carries.

The carrier used in the trial is likely to be Ringer's salts—however this may differ from the carrier used in the final commercial formulation.

The full cationic fraction and additives are being used for the trial.

A repeat milk growth curve experiment is to be used to determine the desired final concentration.

The concentrations to be used are as follows (these may be higher than the final formulation):

Cationic fraction: 50-84 mg/ml

NaSCN: 20-100 ppm

Ascorbate: 20-100 ppm

Monoglycerol: 5-20 ppm

Size of dose is to be 10 ml, and will aim for 3 doses

Will focus on *Streptococcus uberis* sub-clinical mastitis initially, will also possibly look at *Staphylococcus aureus*.

Will initially look at 15 cases of sub clinical *Streptococcus uberis* mastitis to ensure at least 10 valid treatment subjects.

Selection criteria—no exclusions will be made on lactation stage, age or breed.

Aspects of the present invention have been described by way of example only and it should be appreciated that modifications and additions may be made thereto without departing from the scope thereof.

REFERENCES

Bramley, A. J., Dodd, F. H. 1984. Reviews on the progress of dairy science—Mastitis Control. J. Dairy. Res. 51: 481-512

Dillehay D. L., Webb S. J., Schmelz E.-M., Merrill A. H. Jr. Dietary sphingomyelin inhibits 1,2-dimethylhydrazine-induced colon cancer in CF1 mice. J. Nutr., 1994; 124: 615-620

Merrill, A. H., Schmelz, E-M., Wang, E., Dillehay, D. L., Rice, L. G., Filmore Meredith, and Riley, R. T. Importance of Sphingolipids and Inhibitors of Sphingolipid Metabolism as Components of Animal Diets. The Journal of Nutrition. 127 (5) May 1997. 830S-833S Isaacs C. E., Litov R. E., Thormar H. 1995. Antimicrobial activity of lipids added to human milk, infant formula, and bovine milk. Journal of Nutritional Biochemistry. 6: 362-366

Kussendrager, K. D. and van Hooijdonk, A. C. M. 2000. Lactoperoxidase: physico-chemical properties, occurrence, mechanism of action and applications. British Journal of Nutrition 84: Suppl. 1, S19-S25

Malinowski, E., Klossowska, A., Kaczmarowski, M., Lassa, H., and Kuzma, K. 2002. Antimicrobial Susceptibility of Staphylococci Isolated from Affected with Mastitis Cows. Bull. Vet. Inst. Pulawy. 46: 289-294

Merrill, A. H., Jr. & Sweeley, C. C. (1996) Sphingolipid metabolism and cell signalling. In: New Comprehensive Biochemistry: Biochemistry of Lipids, Lipoproteins, and Membranes (Vance, D. E. & Vance, J. E., eds.), pp. 309-338. Elsevier Science, Amsterdam, The Netherlands Newburg, D. S., 1996. Oligosaccharides and glycoconjugates in human milk: their role in host defense. J. Mann. Gland Biol. Neoplasia 1, 271-282.

Reiter, B and Oran, J. D. 1967. Bacterial inhibitors in milk and other biological fluids. *Nature* (Lond.) 216: 328-33

Schanbacher, F. L., Smith, K. L. 1975. Formation and role of unusual whey proteins and enzymes: relation to mammary function. J. Dairy Sci. 58: 1048-1062

Smolenski, G., Haines, S., Kwan, F. Y.-S., Bond, J., Farr, V., Davis, S. R., Stelwagen, K. and Wheeler, T. 2007. Characterisation of Host Defence proteins in Milk using a Proteomic approach. J. Proteome Research 6 (1):207-215

Talhouk, R. S., Neiswander, R. L., Scanbacher, F. I. 1996. Developmental regulation and partial characterization of growth factors in the bovine mammary gland. J. Repro. Fert. 106: 221-230

What I claim is:

1. A method of treating a microbial infection caused by gram-positive bacteria or gram-negative bacteria in a mammal in need thereof comprising administering a formulation, the formulation including a therapeutically effective amount of a cationic fraction that has been eluted from whole milk, processed milk or whey, wherein the cationic fraction comprises:
   a. a component selected from the group consisting of cathelicidin-1 and serum amyloid A protein;
   b. chitinase-like protein (CLP-1); and
   c. lactoperoxidase, angiogenin, quiescin, jacalin-like protein and lactoferrin all of which are from the cationic fraction; and
   d. a mixture of cationic peptides all of which are from the cationic fraction,
   wherein the formulation is adapted to be applied directly onto or into a site of microbial infection.

2. The method of claim 1, wherein the microbial infection is caused by at least one of *Streptococcus uberis, Staphylococcus aureus* or *Escherichia coli*.

3. The method as claimed in claim 1 for the treatment of bovine mastitis.

4. The method of claim 1, wherein the method is used for treating mastitis in a cow during a drying off or a dry period.

5. The method of claim 1, wherein the method is used for treating mastitis in a cow during a lactation period.

6. The method of claim 1 wherein the method includes applying the formulation onto or into at least one bovine teat.

7. The method of claim 1, wherein the formulation includes one or more of the following:
   a. a peroxidase substrate source being sodium thiocyanate, and/or
   b. a hydrogen peroxide source being ascorbate or ascorbic acid.

8. The method of claim 1, wherein the formulation includes one or more of the following: N-acetyl glucosaminidase, β defensin, lysozyme, at least one immunoglobulin or at least one growth factor.

9. The method of claim 1, wherein the formulation includes one or more of the following: antibiotics, analgesics, carriers, buffers, preservatives, excipients, controlled release components, hardening or any other pharmaceutically acceptable component.

10. The method of claim 1, wherein the formulation includes a cell lysing substance.

11. The method of claim 1, wherein the formulation includes a detergent, monoglyceride and/or monolauryl glycerol.

* * * * *